(12) United States Patent
Stien et al.

(10) Patent No.: US 9,186,168 B2
(45) Date of Patent: Nov. 17, 2015

(54) MEDICAL INSTRUMENT AND METHOD OF CUTTING A TISSUE USING THE MEDICAL INSTRUMENT

(71) Applicant: Stewart and Stien Enterprises, LLC, Eau Claire, WI (US)

(72) Inventors: Karl E. Stien, Eau Claire, WI (US); Nathaniel J. Stewart, Eau Claire, WI (US)

(73) Assignee: Stewart and Stein Enterprises, LLC, Eau Claire, WI (US)

( * ) Notice: Subject to any disclaimer, the term of this patent is extended or adjusted under 35 U.S.C. 154(b) by 0 days.

(21) Appl. No.: 14/494,118

(22) Filed: Sep. 23, 2014

(65) Prior Publication Data

US 2015/0012024 A1    Jan. 8, 2015

Related U.S. Application Data

(63) Continuation-in-part of application No. 13/889,561, filed on May 8, 2013.

(60) Provisional application No. 61/953,063, filed on Mar. 14, 2014.

(51) Int. Cl.
*A61B 17/32* (2006.01)
*A61B 17/3205* (2006.01)
*A61B 18/14* (2006.01)
*A61B 18/00* (2006.01)

(52) U.S. Cl.
CPC ........... *A61B 17/3205* (2013.01); *A61B 18/148* (2013.01); *A61B 2017/320044* (2013.01); *A61B 2018/00595* (2013.01); *A61B 2018/00601* (2013.01); *A61B 2018/1412* (2013.01); *A61B 2018/1422* (2013.01)

(58) Field of Classification Search
CPC ..................... A61B 18/04; A61B 2017/00349; A61B 2017/00353; A61B 2017/00358; A61B 17/3205; A61B 18/148; A61B 2017/320044; A61B 2018/00595
USPC .............................................. 606/37, 39, 182
See application file for complete search history.

(56) References Cited

U.S. PATENT DOCUMENTS

| | | | |
|---|---|---|---|
| 6,254,620 B1 * | 7/2001 | Koh et al. ...................... 606/167 |
| 2009/0182332 A1 * | 7/2009 | Long et al. ...................... 606/51 |
| 2011/0054461 A1 * | 3/2011 | Dickhans ........................ 606/33 |

* cited by examiner

*Primary Examiner* — Christopher D Koharski
*Assistant Examiner* — Michael Carey
(74) *Attorney, Agent, or Firm* — Wood, Phillips, Katz, Clark & Mortimer

(57) ABSTRACT

A medical instrument having an elongate frame with proximal and distal ends spaced in a lengthwise direction along a central axis. A working assembly at a distal region of the frame has a U-shaped portion defined by first and second legs meeting at a base. The U-shaped portion defines a cutting space. The working assembly further has a cutting assembly with a sharp edge in the cutting space. The working assembly and elongate frame are configured so that a tissue entryway is defined through which a tissue can be advanced to be moved into the cutting space and against the sharp edge. The medical instrument further has a first assembly configured to be operated to vary a configuration of the entryway.

21 Claims, 11 Drawing Sheets

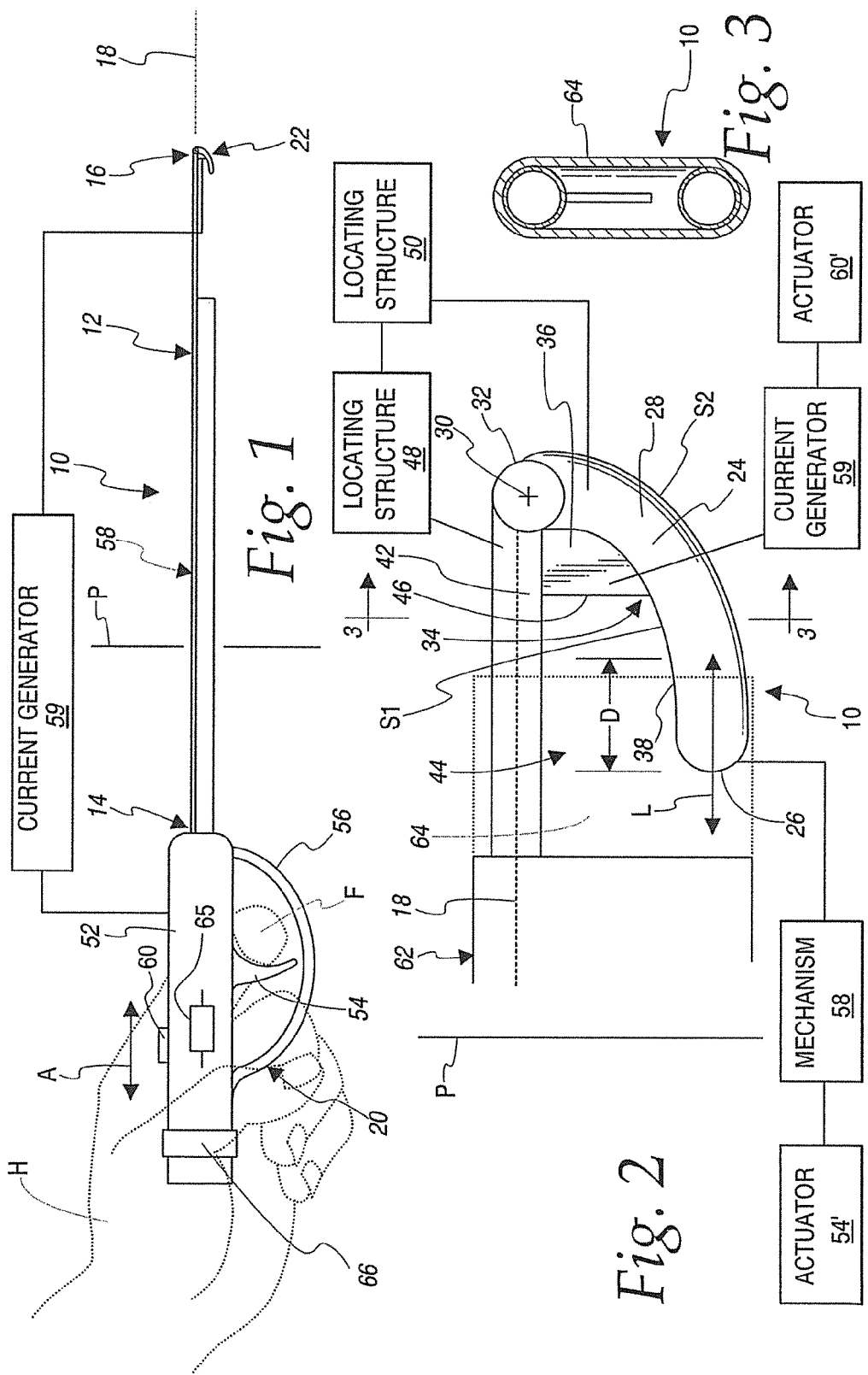

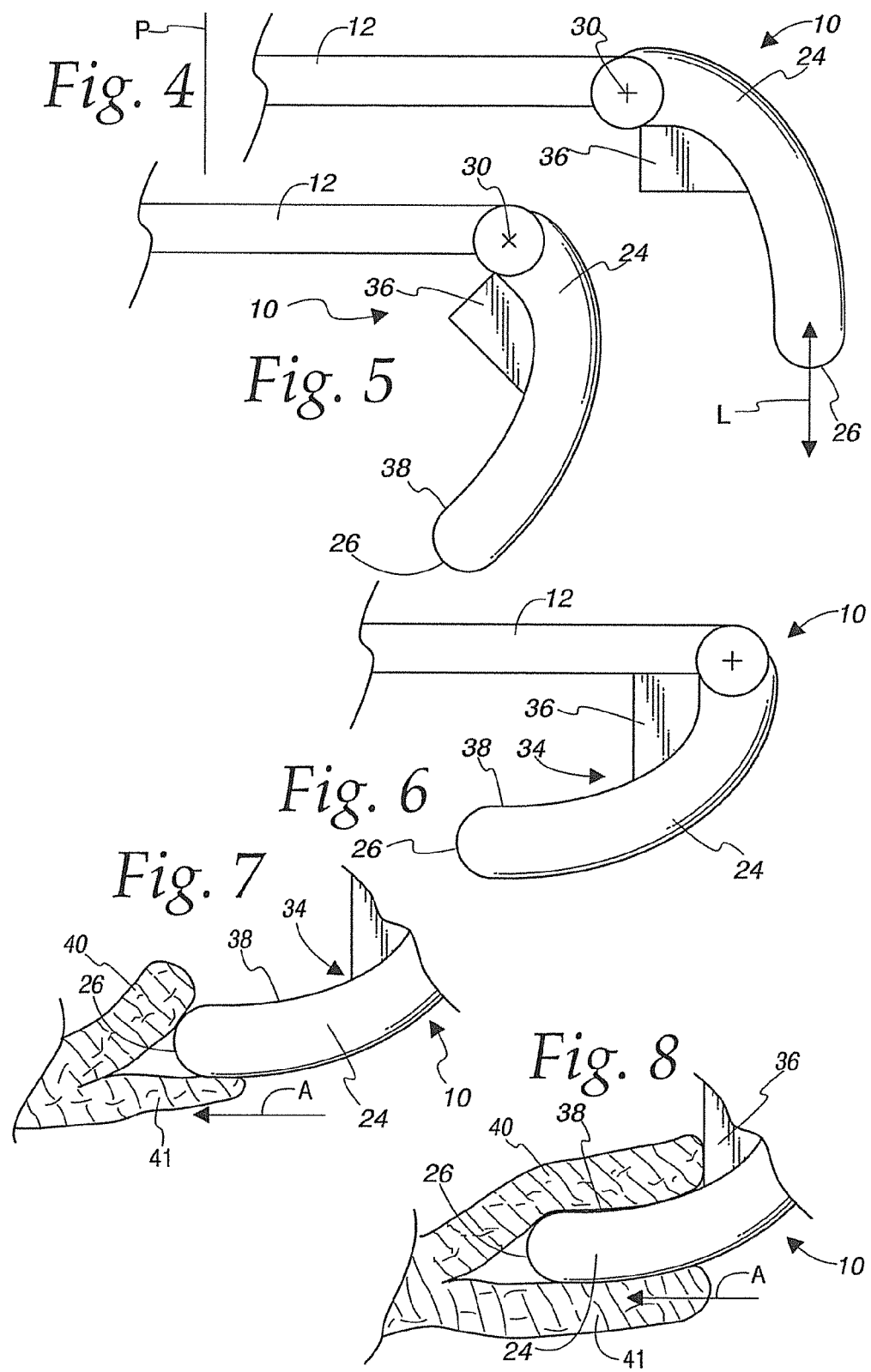

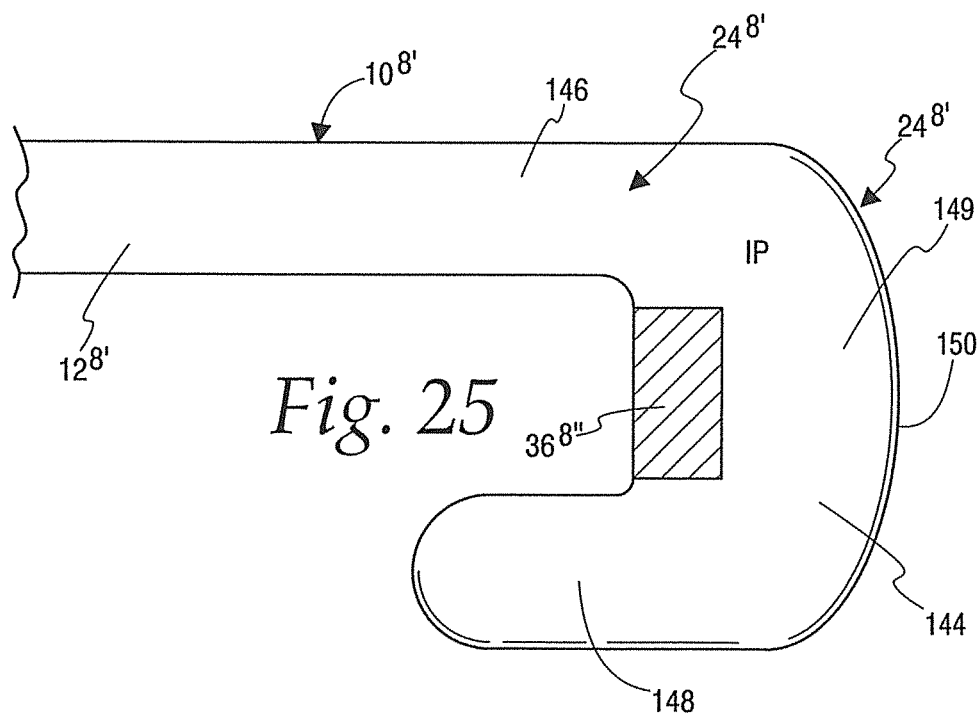
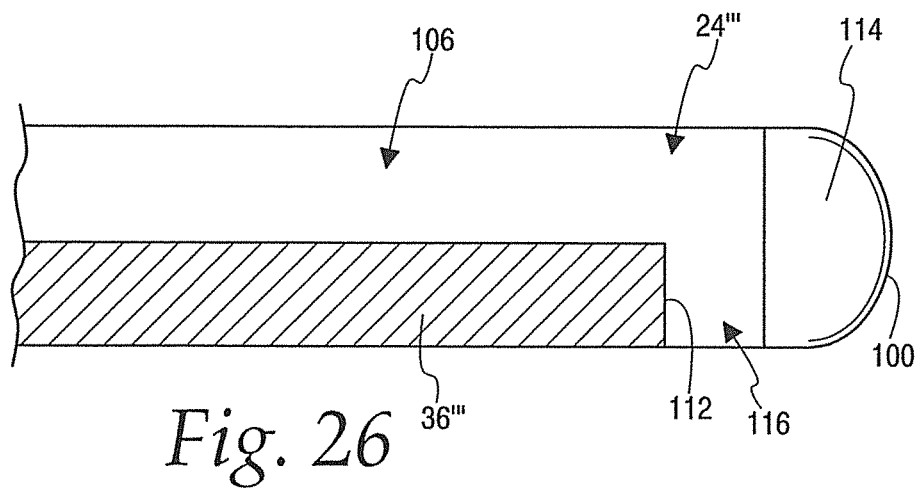
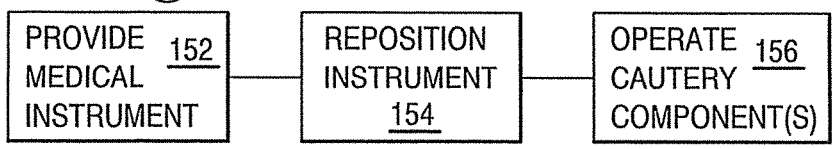

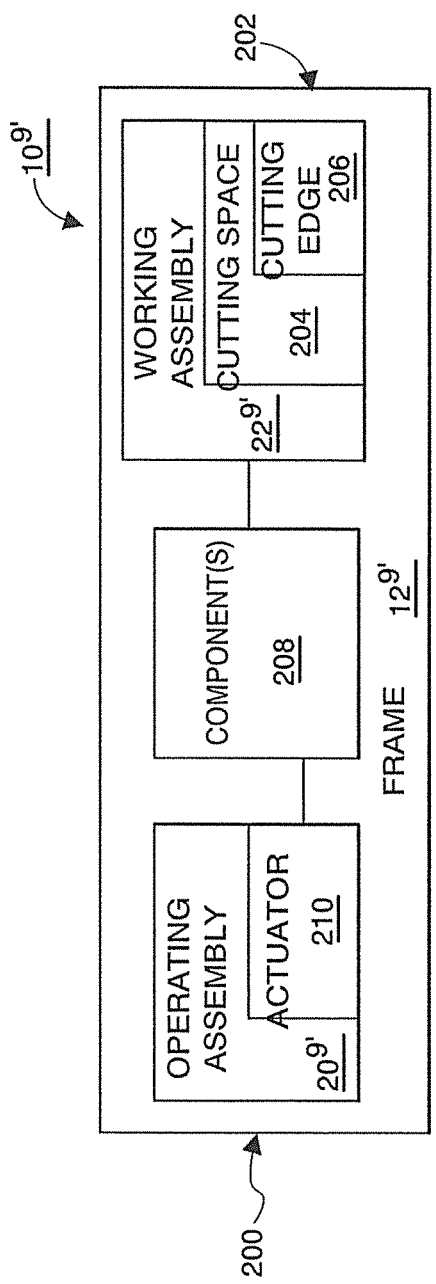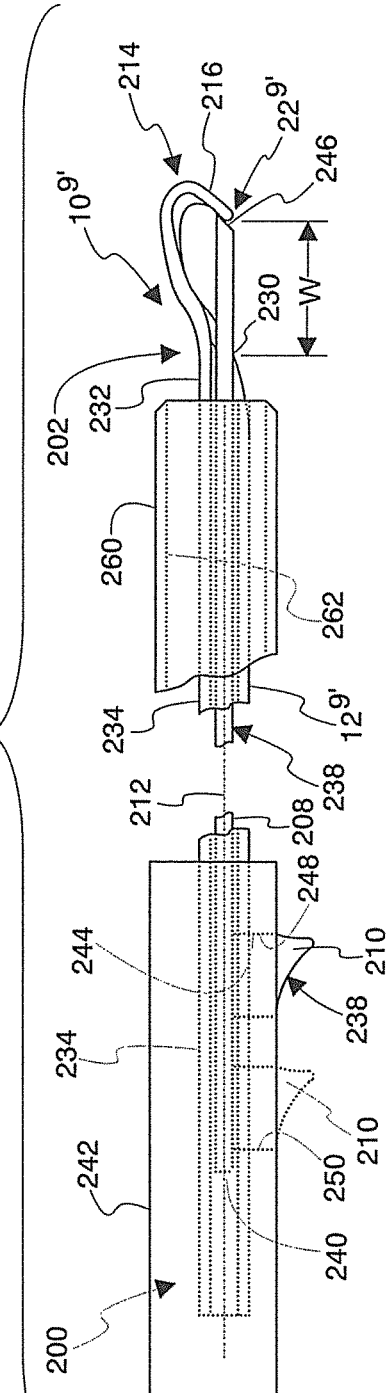

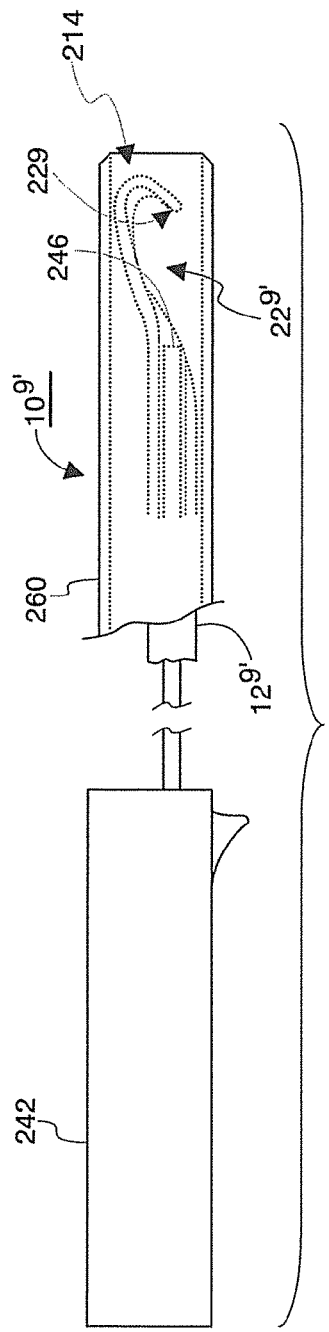
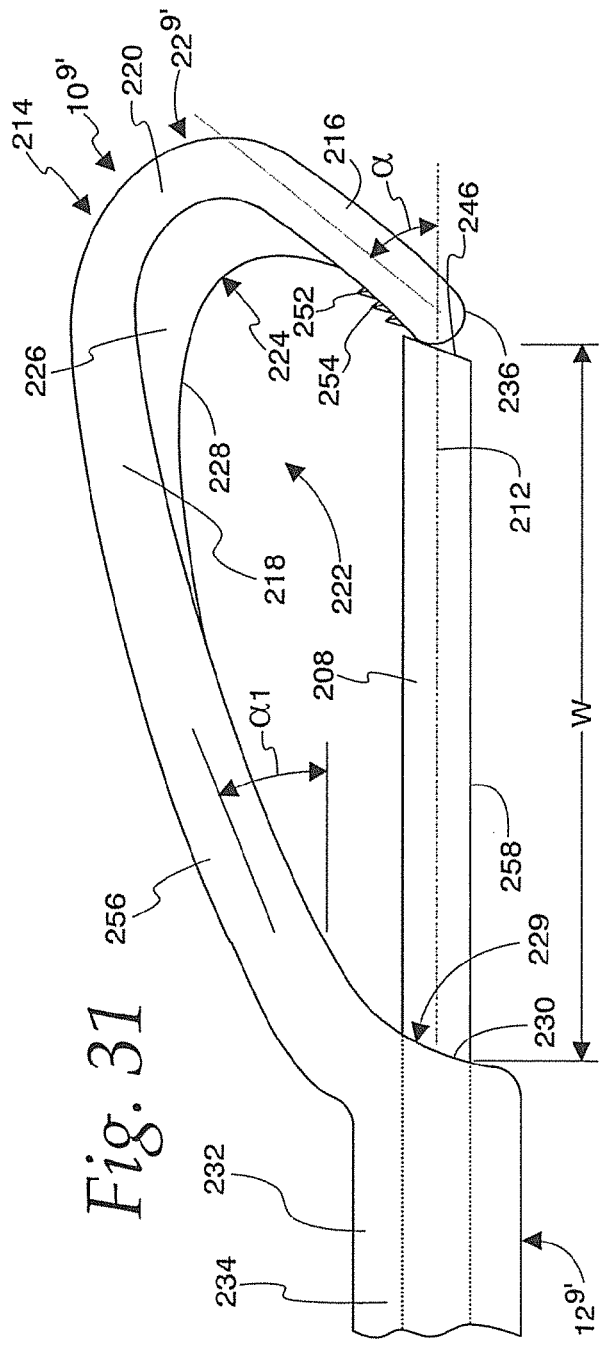

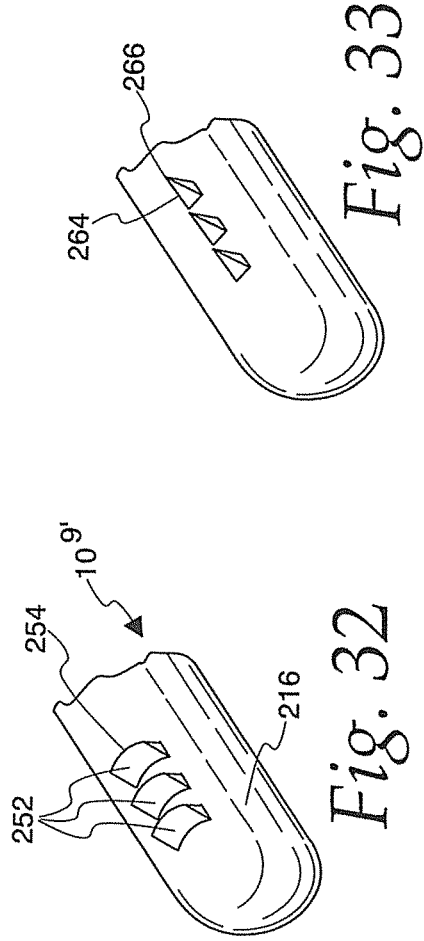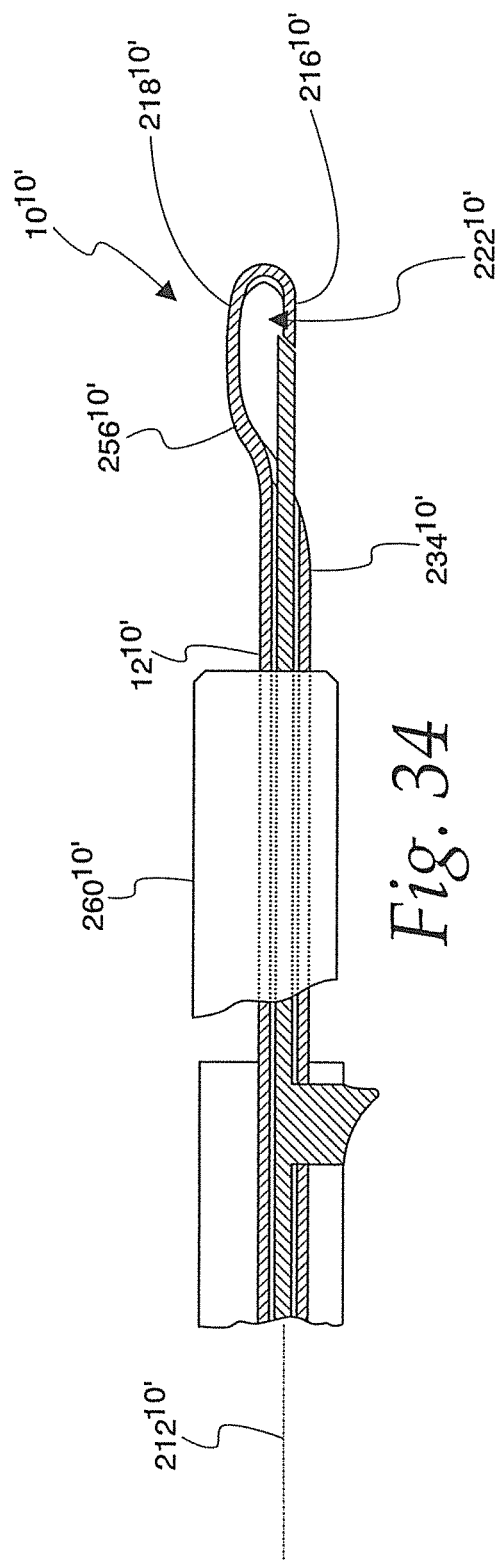

MEDICAL INSTRUMENT AND METHOD OF CUTTING A TISSUE USING THE MEDICAL INSTRUMENT

CROSS-REFERENCE TO RELATED APPLICATIONS

This application is a continuation-in-part of, and claims priority to, provisional application U.S. Ser. No. 61/953,063, filed Mar. 14, 2014, and U.S. Ser. No. 13/889,561, filed May 8, 2013, both of which are hereby incorporated by reference in their entirety.

BACKGROUND OF THE INVENTION

1. Field of the Invention

This invention relates to medical instruments and, more particularly, to a medical instrument for repositioning and cutting a human body tissue at an operating site. The invention is also directed to a method of using such a medical instrument.

2. Background Art

In many surgical procedures, tissue is required to be controllably dissected. This dissection is commonly effected using cauterization. Oftentimes, the dissection is effected using only a blade with a sharp cutting edge that is drawn against the region of the tissue to be cut.

While it is known to manipulate tissue through an instrument having a hooked distal end at which a cutting blade is located, heretofore there have been a number of limitations associated with this basic instrument configuration.

As one example, U.S. Pat. No. 5,397,333 (Knoepfler) discloses an instrument wherein a sharp cutting blade is defined in a cutting space within the curvature of a hooked end. During introduction into, and movement of the hooked end within a cavity, tissue may be inadvertently brought into contact with the exposed cutting blade. This can lead to collateral damage around the intended site and may lengthen procedure times and potentially necessitate internal treatment of tissue to repair inadvertently cut regions thereof.

While use of a cannula may shield tissue from the cutting blade as the instrument is initially directed towards an operating site, the potential for collateral damage arises again, after the cannula is removed, as a surgeon relocates the hooked end to different sites as a procedure may demand. Further, damage may be inflicted at the conclusion of a procedure as the instrument, with the exposed cutting blade, is withdrawn.

Additionally, once the desired tissue portion is strategically situated in the cutting space preparatory to effecting a cut, the tissue has a tendency to escape from the cutting space. That is, the guiding inside surface of the hooked region, which is generally smooth, allows free sliding of the tissue therealong which could precipitate separation of the targeted tissue from the instrument. This may necessitate repeating steps, which adds undesirably to the overall time necessary to perform the procedure.

Further, uncontrolled tissue movement relative to the hooked end may make it difficult, or impossible, to precisely locate a cut.

The industry continues to seek better designs for instruments of this type, focused on at least the aforementioned limitations of existing designs.

SUMMARY OF THE INVENTION

In one form, the invention is directed to a medical instrument having an elongate frame with proximal and distal ends spaced in a lengthwise direction along a central axis of the frame and a working assembly at a distal region of the frame. The working assembly has a U-shaped portion defined by first and second legs meeting at a base. The U-shaped portion opens toward the proximal end of the elongate frame and defines a cutting space. The working assembly further includes a cutting assembly with a sharp edge in the cutting space to be pressed against a tissue to effect cutting thereof. The working assembly and elongate frame are configured so that a tissue entryway is defined through which a tissue can be advanced to be moved into the cutting space and against the sharp edge. The medical instrument further includes a first assembly configured to be operated to vary the configuration of the entryway.

In one form, the entryway has a width dimension substantially parallel to the central axis of the frame. The first assembly is configured to vary the width of the entryway.

In one form, the first assembly has a first component that is advanced in a direction substantially parallel to the central axis of the frame to vary the width of the entryway.

In one form, the medical instrument further includes an operating assembly with an actuator on the frame at a location spaced from the working assembly towards a proximal end of the frame. The actuator is configured so as to be operable to move the first component in an operating path in opposite directions substantially parallel to the central axis of the frame.

In one form, the first leg of the U-shaped portion has a free end. The first component is advanced selectively towards and away from the free end of the first leg to respectively decrease and increase the width of the entryway.

In one form, the first component has a free end that can be moved to reside at or adjacent to the free end of the first leg to substantially block the width of the entryway.

In one form, the first component is in the form of an elongate rod with an axis that is substantially parallel to the central axis of the frame.

In one form, the first leg projects in a line that is substantially parallel to the central axis of the frame. The line is one of: a) coincident with; or b) adjacent to the central axis of the frame.

In one form, the cutting edge is located at the base of the U-shaped portion.

In one form, the first and second legs project in substantially parallel lines that are substantially parallel to the central axis of the frame.

In one form, at least one discrete component is provided on at least one of the first and second legs and configured to inhibit sliding of tissue against and along the at least one of the first and second legs.

In one form, the one of the first and second legs has a free end. The one discrete component projects away from the free end.

In one form, the at least one discrete component has a sharp free end.

In one form, the at least one discrete component in the form of a pair of spaced ribs.

In one form, the medical instrument is provided in combination with a cannula with an internal passage within which at least a part of the working assembly resides with the cannula and medical instrument in a first relationship. The cannula and medical instrument are movable relative to each other to change from the first relationship into a second relationship wherein at least a portion of the part of the working assembly is exposed outside of the cannula.

In one form, the frame has an elongate shaft with a first length that is substantially parallel to the central axis. The central axis of the frame extends through the elongate shaft. A transition section connects between the first length and second leg.

In one form, the free end of the first leg is blunt so as not to readily cut through tissue bearing against the end of the first leg as tissue is engaged and manipulated by the medical instrument.

In one form, the sharp edge on the cutting assembly has a curved shape.

In one form, the first leg projects in a straight line that makes an angle of between 30° and 60° with the central axis of the frame.

In one form, the invention is directed to a method of cutting a human tissue. The method includes the steps of: providing the medical instrument described above; engaging the free end of the first leg with the tissue; progressively moving the medical instrument relative to the tissue so that part of the tissue is: a) moved into the cutting space and against the sharp edge of the cutting assembly; and b) engaged by the at least one discrete component so that the at least one discrete component resists sliding movement of the part of the tissue out of the cutting space; and with the tissue against the sharp edge, drawing the sharp edge against the part of the tissue to effect cutting thereof.

BRIEF DESCRIPTION OF THE DRAWINGS

FIG. 1 is a side elevation view of one form of medical instrument, according to the present invention, and made up of an elongate frame with operating and working assemblies, respectively at proximal and distal regions thereof;

FIG. 2 is an enlarged, fragmentary, elevation view of the working assembly on the medical instrument in FIG. 1, and a repositionable tip thereon, with the tip in a first position;

FIG. 3 is a cross-sectional view of the working assembly taken along line 3-3 of FIG. 2;

FIG. 4 is an enlarged, fragmentary, elevation view of the medical instrument, as in FIG. 2, and showing the tip in a second position;

FIG. 5 is a view as in FIG. 4 with the tip moved to another position between the first and second positions;

FIG. 6 is a view as in FIGS. 4 and 5 with the tip moved from the second position to and past the FIG. 5 position to the first position, as shown also in FIG. 2;

FIG. 7 is an enlarged, fragmentary, elevation view of the medical instrument showing the tip engaging a tissue portion preparatory to cauterization with the tip in the first position, shown in FIGS. 2 and 6;

FIG. 8 is a view as in FIG. 7 wherein the tip and tissue portion have been relatively moved to place the tissue portion at a cutting location against a cautery device on the working assembly while maintaining the tip in the first position;

FIG. 25 is a view as in FIG. 24 of a still further modified form of medical instrument, according to the invention;

FIG. 26 is a fragmentary view showing a leading end of the medical instrument of FIG. 20 with a modification thereto;

FIG. 27 is a flow diagram representation of a method of performing a surgical procedure according to the present invention and utilizing the medical instruments as shown, for example, in FIGS. 19-26;

FIG. 28 is a schematic representation of a further modified form of medical instrument, according to the invention;

FIG. 29 is a fragmentary, side elevation view of one specific form of medical instrument, shown schematically in FIG. 28, and with the medical instrument in a first state in which tissue is blocked from contacting a cutting edge on the medical instrument;

FIG. 30 is a view as in FIG. 29 wherein the medical instrument has been changed to a different state wherein the cutting edge is exposed and with the distal end of the instrument shown within an optional cannula;

FIG. 31 is an enlarged, fragmentary view of the distal region of the medical instrument in the state shown in FIG. 29;

FIG. 32 is an enlarged, fragmentary, perspective view of a leg on the medical instrument in FIGS. 29-31 and with components thereon that prevent slippage of tissue;

FIG. 33 is a view as in FIG. 32 with a modified form of components;

FIG. 34 is a view as in FIG. 29 of a modified form of medical instrument, according to the invention, in a state as shown in FIG. 29;

DETAILED DESCRIPTION OF THE PREFERRED EMBODIMENT

Figure 9:
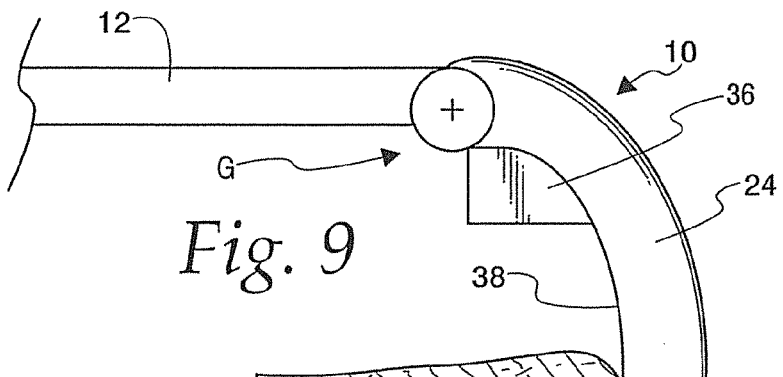
FIG. 9 is a view as in FIGS. 7 and 8 wherein the tip is placed in the second position upon initially engaging a tissue portion.

In FIGS. 1-11, a medical instrument, according to the present invention, is shown at 10. The medical instrument 10 consists of an elongate frame 12 with proximal and distal ends 14, 16, respectively, spaced in a lengthwise direction along a central axis 18 of the frame 12.

An operating assembly 20 is provided at a proximal region of the frame 12. A working assembly 22 is provided at a distal region of the frame 12.

The working assembly 22 consists of a cantilevered tip 24 with a free end 26. The tip 24 has a body 28. The working assembly 22 is reconfigurable by an operator through the operating assembly 20 by selectively reorienting the tip 24 relative to the frame 12. In the depicted embodiment, the tip body 28 is movable relative to the frame 12 around a fixed axis 30.

The various contemplated positions for the tip 24 can also be clearly described relative to a reference plane P that extends through the frame 12 orthogonally to the central axis 18 at a location on the frame 12 spaced axially from the working assembly 22 toward the operating assembly 20. The location of the reference plane P in FIG. 1 is not limited to what is shown.

The body 28 of the tip 24 has a continuously curved shape between the rounded free end 26 and axis 30. The body 28 may be locally narrowed between the free end 26 and axis 30, as shown in dotted lines in FIG. 2, for reasons explained below. While the body 28 has a continuous curve, for purposes of the description and claims herein, the tip 24 will be characterized as "projecting" in a direction that is substantially along a line L, indicated by the double-headed arrow in FIGS. 2 and 4, which is generally parallel to a discrete length of the body 28 extending from the free end 26 a distance D towards the opposite body end 32.

The tip 24 is movable in a range between a first position, as shown in FIG. 2, and a second position, as shown in FIG. 4. The actual range could be less than that shown or greater than that shown, but is preferably selected so that the tip 24 can be placed in at least the first and second positions depicted.

In one position within this range, which is shown in the exemplary form as the first position, the tip 24 projects in a first axial direction toward the reference plane P to allow the tip free end 26 to be engaged, as with a tissue portion at an operation site, and controllably moved through the instrument guidingly along the tip to a cutting location at 34.

The medical instrument 10 is designed to manipulate and dissect tissue and other potentially human body parts. For purpose of the detailed description and claims, "body part" will be used to encompass any part of the human body that can be engaged by the medical instrument, with the depicted or like configuration, so that a portion thereof can be situated at the cutting location 34 whereat it can be dissected, as described below.

At the cutting location 34, at least one cautery component 36 is provided. In this embodiment, there is a single cautery component 36. The cautery component 36 contacts the body part at the cutting location 34 and is operable to generate a current that heats a contacted portion of the human body part at the cutting location 34.

By reason of the shape of the tip body 28, the instrument 10 can be manipulated so as to readily and consistently place a portion of the subject body part predictably at the cutting location 34 in an orientation to dissect across a desired cutting plane. More specifically, the tip body 28 has a surface portion 38 that curves progressively from the convex/rounded tip free end 26 up to the cutting location at 34. With the dotted line configuration of FIG. 2, the body 28 is slightly bulbous adjacent to the free end and tapers in diameter away therefrom so as not to inhibit guided sliding movement of a body part portion therealong. The surface portion 38 is also slightly concavely curved over this body length to facilitate this sliding movement of the portion of the body part thereagainst.

As seen in FIGS. 7 and 8, as the tip 24 encounters a body part portion 40, such as tissue, at the operation site, advancement of the instrument 10 in the direction of the arrow A causes the portion 40 to be drawn upwardly, as away from bone and/or another body part portion 41 at the operation site, and move guidingly up the free end 26 to the surface portion 38. Continued advancement of the instrument 10 in the direction of the arrow A causes the portion 40 to arrive at the cutting location 34, whereat it encounters the cautery component 36. In FIGS. 7 and 8, the tip 24 is in the first position therefor, as shown in FIGS. 2 and 6, though the same steps can be performed with the tip 24 in other positions.

The body 28 is preferably made from a material that is not electrically conductive, such as a plastic or other non-metal material, over those surface portions, as shown at S1, S2, that are exposed to potentially contact tissue during procedures. The entire body 28 may be made to be non-conductive. Ideally, as the instrument 10 engages body parts during a procedure, the surfaces on the instrument 10 that contact the body parts will not conduct electricity with the cautery component 36 energized. This minimizes the inadvertent infliction of any damage upon any body tissue or other body part other than the body part intended to be contacted by the cautery component 36. Thus, during cauterization, surrounding tissue can be insulated from the cautery component 36 to thereby minimize collateral damage inflicted by heat generated by the energized cautery component 36.

In this embodiment, a distal portion 42 of the frame 12 and the tip body 28 cooperatively define a "U" shape opening axially in a first direction toward the operating assembly 20. With this arrangement, pressure application upon the instrument 10 in the first axial direction causes the body part portion 40 to become captively blocked in a space at 44. The frame portion 42 and tip 24 define spaced legs of the "U" bounding that space 44. The width of the space 44 narrows slightly towards the cutting location with the tip 24 in its first position so that the body part portion 40 is consistently funneled to against the cautery component 36. So long as pressure is maintained on the instrument 10 in the direction of the arrow A, the body part portion 40 will not escape from the space 44.

Additionally, the distal portion 42 of the frame 12 can be made with a non-conductive material to be even more certain that no damage will be inflicted upon the body part portion 40 other than at the intended cauterization site. With this construction, the entire "U" shape on the working assembly 22 is electrically insulated as it engages surrounding body parts as the cautery component 36 is brought into contact with a body part region to be cauterized. The cauterization component 36 may be made, as shown, to span between the frame portion 42 and tip 24 to be consistently brought into contact with the body part portion 40 in a desired plane. In the embodiment shown, the cautery component 36 defines a substantially straight edge 46 that engages the body part portion 40 at the cutting location 34. The edge 46 is shown to extend fully and continuously between the tip 24 and frame portion 42. While the edge 46 is shown as straight, this is not a requirement, nor is it a requirement that there be a single component that produces the cauterization energy. Further, the edge 46 need not be continuous as shown.

Figure 10:
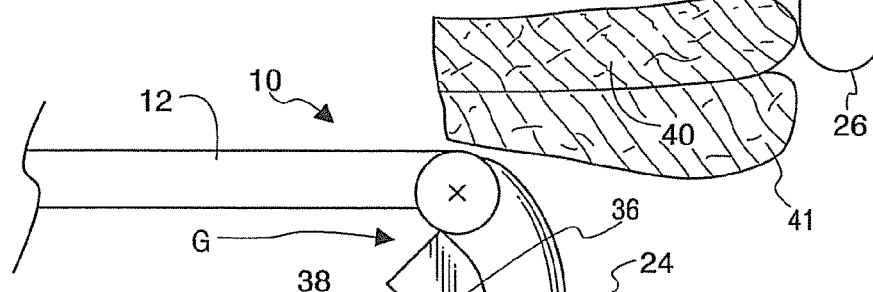
FIG. 10 is a view as in FIG. 9 wherein the tip is repositioned to guide the tissue portion towards the cutting location.

The process of dissecting the particular body part portion 40 may be initiated with the tip 24 in the first position therefor, as shown in FIG. 6, wherein the line of the tip 24 is substantially parallel to, and spaced radially from, the frame axis 18. Alternatively, the angle of projection of the tip 24 can be changed depending upon the particular application and geometry at the operation site. For example, the projecting line L of the tip 24 may be as shown in FIGS. 4 and 9, representing the aforementioned second position, wherein the tip projecting line is substantially parallel to the reference plane P. The cauterization process could be carried out with this tip position maintained. Alternatively, the tip 24 might be repositioned to a third position, as shown in FIGS. 5 and 10 or back into the first position in FIGS. 4 and 9. As the position of the tip 24 changes, the body part portion 40 is guidingly slid along the surface portion 38 to against the edge 46 at the cutting location 34.

Figure 11:
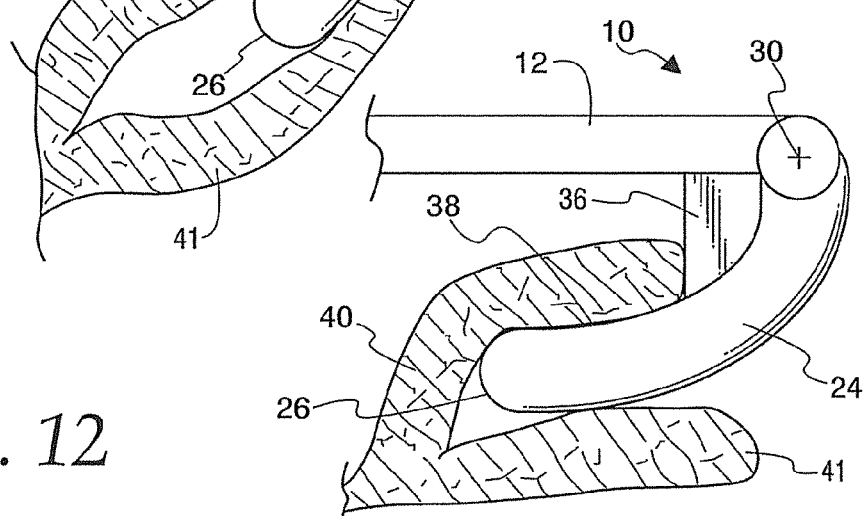
FIG. 11 is a view as in FIGS. 9 and 10 wherein the tip is moved to the first position whereby the tissue portion is moved fully to the cutting location.

Referring to FIGS. 9-11, with the tip 24 initially in the FIG. 9 position, the free end 26 can be situated at the interface between the body part portions 40, 41. Movement of the tip 24 toward the FIG. 11 position wedges the body part portion 40 away from the body part portion 41, as seen in FIG. 10, until the body part portion 40 is eventually situated to engage the cautery component 36, as seen in FIG. 11.

By reason of making exposed surfaces on the tip 24 non-conductive, the body part portion 41 remains at all times electrically insulated from the cautery component 36.

Cooperating locating structure, shown schematically at 48, 50, may be provided respectively on the frame 12 and tip 24 to allow the first and second positions, and potentially the third and other desired tip positions, to be consistently set and releasably maintained. The cooperating locating structure 48, 50 may be a detent-type of arrangement or take the form of another type of component known to those skilled in the art, or devisable thereby.

The operating assembly 20 is shown to include a graspable handle portion 52 around which a surgeon's fingers can be wrapped to firmly hold the instrument 10 and allow comfortable manipulation thereof. A trigger/actuator 54 is shown in FIG. 1 and is engageable and movable, as in the direction of the arrow AA, by a finger F on the hand H that is wrapped around the graspable handle portion 52 to controllably reposition the tip 24. A U-shaped, protective cage 56 shields the trigger region and the fingers that operate the trigger 54, thereby avoiding an inadvertent contact that might cause an unintended movement of the trigger 54 by the surgeon during a procedure.

A mechanism is shown at 58, partially within the frame 12, for converting movement of the trigger 54 into a force that causes pivoting of the tip 24. Many different suitable mechanisms 58 could be devised by one skilled in the art. Thus there is no need herein to discuss details of such structure.

The invention also contemplates other types of actuators for the mechanism 58, as shown generically at 54' in FIG. 2.

The cautery component 36 is energized by a current generator 59 of conventional construction. The current generator 59 is operable by a switch actuator 60 that is translatable along the line of the double-headed arrow AA between "on" and "off" positions and potentially to vary operating current.

The current generator 59 can be operated through other types of actuators. A generic actuator 60' is shown in FIG. 2 and may be in the form of a foot pedal or other type of mechanism.

Another optional feature is the provision of a cover assembly at 62. The cover assembly 62 consists of a sleeve 64 with a generally oval cross-sectional shape, as shown in FIG. 3, to slide over a portion of the tip 24, with the tip 24 in its first position and the cover assembly 62 in a covering state. The sleeve 64 can be retracted to the solid line position in FIGS. 1 and 2 into a retracted state wherein the tip 24 is fully exposed. The sleeve 64 can be repositioned through an actuator 65 on the handle 52. The actuator 65 is shown as a translatable component engageable and movable by the thumb or a finger on a user's hand H, as along a line indicated by the double-headed arrow AA.

By extending fully around the free end 26 of the tip 24 with the tip 24 in its first position, the direction of the working assembly 22 to the operating site, and withdrawal of the same therefrom, is facilitated without snagging of the tip free end 26, whether the procedure is carried out laparoscopically or through an open incision.

An actuator 66 is shown in FIG. 1 in the form of a ring that is journaled for turning relative to the graspable handle 52 about an axis. This actuator 66 design might be used instead of, or in conjunction with, actuators as previously described for the tip 24, the current generator 59 and the cover assembly 62.

Figure 12:
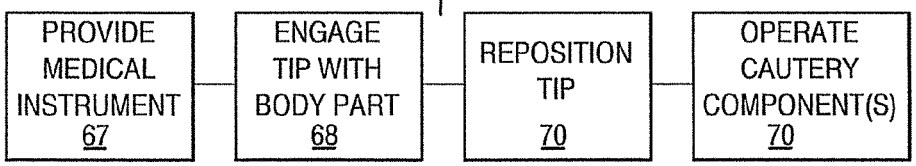
FIG. 12 is a flow diagram representation of a method of performing a surgical procedure according to the present invention.

With the medical instrument 10 as depicted, a method of performing a surgical procedure can be carried out as shown in flow diagram form in FIG. 12.

As shown at block 67, a medical instrument is provided, as described above.

As shown at block 68, the tip is engaged with a body part.

As shown in block 70, the tip is repositioned relative to the portion of the body part by: a) moving the medical instrument relative to the body part; and/or b) repositioning the tip relative to the frame from one position into another position to thereby cause a portion of a human body part to move guidingly along the tip from the free end to the cutting location whereat the portion of the human body part engages the at least one cautery component.

As shown at block 72, the one cautery component is operated to dissect the portion of the body part at the cutting location.

As noted previously, the procedure can be carried out as shown in FIGS. 7 and 8 with the tip engaged and repositioned relative to the body part portion without changing the position of the tip relative to the frame. Alternatively, as shown sequentially in FIGS. 9-11, the tip can be reoriented to effect engagement and repositioning of the body part therealong to present the body part portion at the cutting location. In both cases, the portion of the body part is lifted by, and slid along, the tip.

With the tip 24 positioned as in FIGS. 9 and 10, a gap G is produced that potentially could result in a body part being pinched between the cautery component 36 and frame 12 as the tip 24 moves further towards the FIG. 11 position and ultimately into the FIG. 11 position. While this gap G does not necessarily present a problem, the gap G can be eliminated by modifying the tip configuration.

Figure 13:
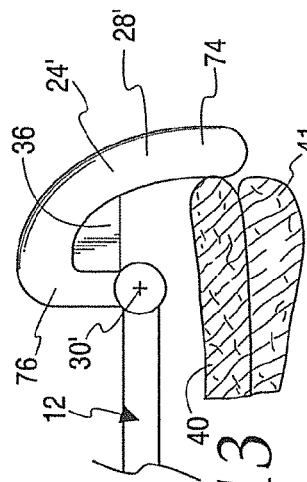
FIGS. 13-15 are views corresponding successively to FIGS. 9-11 and showing a modified form of working assembly, according to the present invention.
Figure 14:
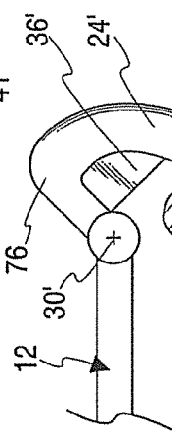
Figure 15:
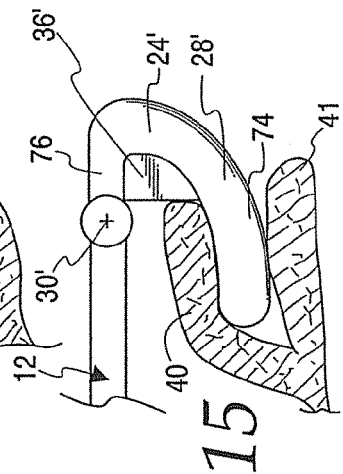

In one modified form, as shown in FIGS. 13-15, a tip 24' is shown with a body 28' having a fixed "U" shape. One leg 74 of the "U" shape defined by the body 28' corresponds to the tip 24, previously described. The other leg 76 is connected to the frame 12 for guided pivoting movement around an axis 30'.

The body 28' is movable between the positions shown in FIGS. 13 and 15, causing the leg 74 to move correspondingly to the tip 24 between the FIG. 4 and FIG. 6 positions.

With the fixed "U" shape, the cautery component 36' is in fixed relationship to, and spans fully between, the legs 74, 76 throughout the range of movement of the body 28'.

As seen in FIGS. 13-15, the leg 74, which becomes a cantilevered "tip", cooperates with the aforementioned body part portions 40, 41 as it is moved between the FIGS. 13 and 15 positions, in the same manner that the tip 24 cooperates with the body part portions 40, 41, as it moves between the FIGS. 9 and 11 positions.

Figure 16:
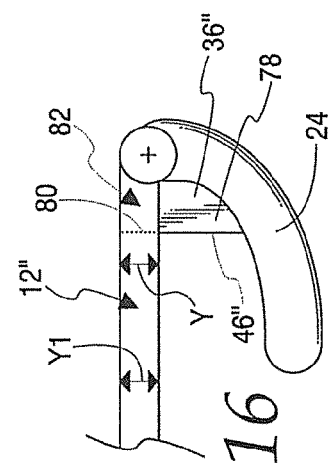
FIG. 16 is a view as in FIG. 11 and showing a modified form of cautery component on the working assembly.

As a further alternative, as shown in FIG. 16, the tip 24 can be used with a modified form of frame 12" and cautery component 36".

The cautery component 36" has a body 78 and a cutting edge 46" thereon with an extended length Y compared to the cautery component 36. The frame 12" has a slot 80 formed therein to accept the extended portion at 82 of the cautery component 36".

Depending upon the dimension Y1 of the frame 12", the aforementioned gap G may be reduced or altogether eliminated using this configuration.

Figure 17:
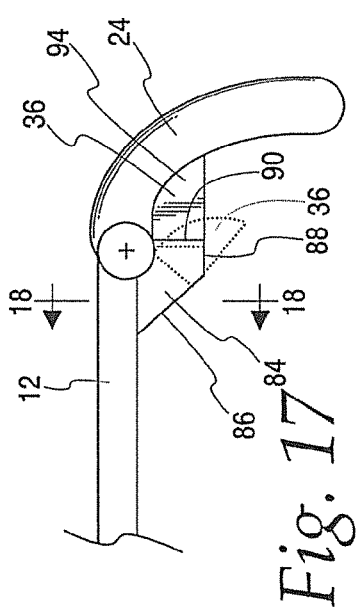
FIG. 17 is a view as in FIG. 9 and showing a modified form of working assembly including a wall that cooperates with a cautery component as the tip thereon is moved over its permissible range.
Figure 18:
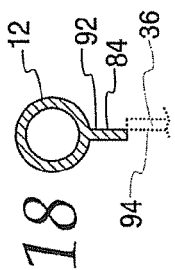
FIG. 18 is a cross-sectional view of the working assembly taken along line 18-18 of FIG. 17.

A still further alternative design is shown in FIGS. 17 and 18. In these Figures, the tip 24, frame 12, and cautery component 36, as described above, are utilized.

A wall 84 is fixed to the frame 12. The wall 84 is generally flat and bounded by straight edges 86, 88, 90 where the wall 84 projects from the frame 12. The plane of one surface 92 of the wall 84 is slightly offset and parallel to a flat surface 94 on the cautery component 36.

The wall 84 may be configured so that the wall 84 and cautery component 36 slide one against the other into different overlapping relationships as the tip 24 is pivoted, thereby to cooperatively span between the tip 24 and frame 12 at all times as the tip 24 is repositioned. Depending upon how the parts are configured, the aforementioned gap G can be either partially or fully eliminated.

Figure 19:
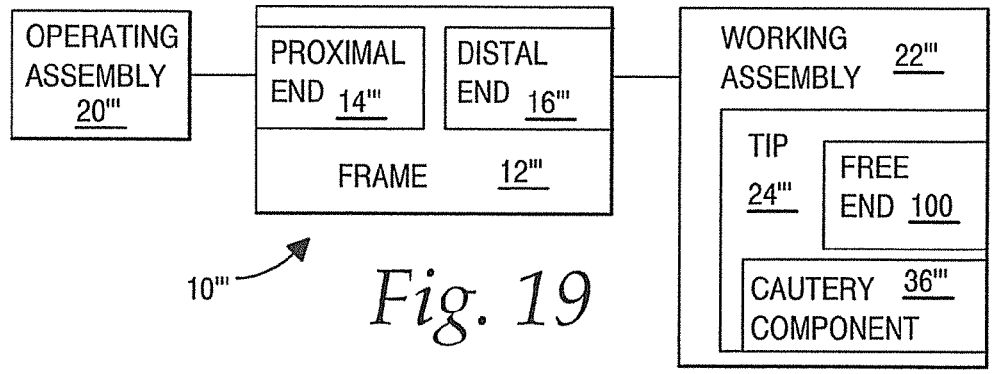
FIG. 19 is a schematic representation of another form of medical instrument, according to the invention.

Referring now to FIG. 19, there is a generic showing of a modified form of medical instrument 10''', with specific embodiments thereof shown in FIGS. 20-26. The medical instrument 10''' consists of an elongate frame 12''' with proximal and distal ends 14''', 16''', respectively. An operating assembly 20''' is provided at a proximal region of the frame 12''', with a working assembly 22''' at a distal region thereof. The medical instrument 10''' differs primarily from those constructions previously described by reason of the fact that the working assembly 22''' has an associated tip 24''' that need not be reconfigurable, although reconfiguration is contemplated. As such, the tip 24''' may essentially be integral with the frame 12''' but, for purposes herein, will be considered to be a separate component. The tip 24''' has a leading free end 100 to be engaged with a human body at an operation site.

The precise construction of the operating assembly 20''' is not critical to the invention. Myriad different designs thereof could be devised by those skilled in this art.

The working assembly 22''' includes at least one cautery component 36''' that may be on, or adjacent to, the tip 24'''. In FIG. 19, the cautery component 36''' is shown as part of the tip 24'''; however, this is not a requirement.

The basic layout and operation of components for the medical instrument 10''' is the same as that for their counterparts in the previously described medical instruments 10, 10', 10". Thus, it is not necessary to re-describe these basic components and their relationships. It suffices to say that on the working assembly 22''', at least one cautery component 36''': a) contacts a human body part at a cutting location; and b) is operable to generate a current that alters a contacted portion of the human body at the cutting location.

Figure 20:
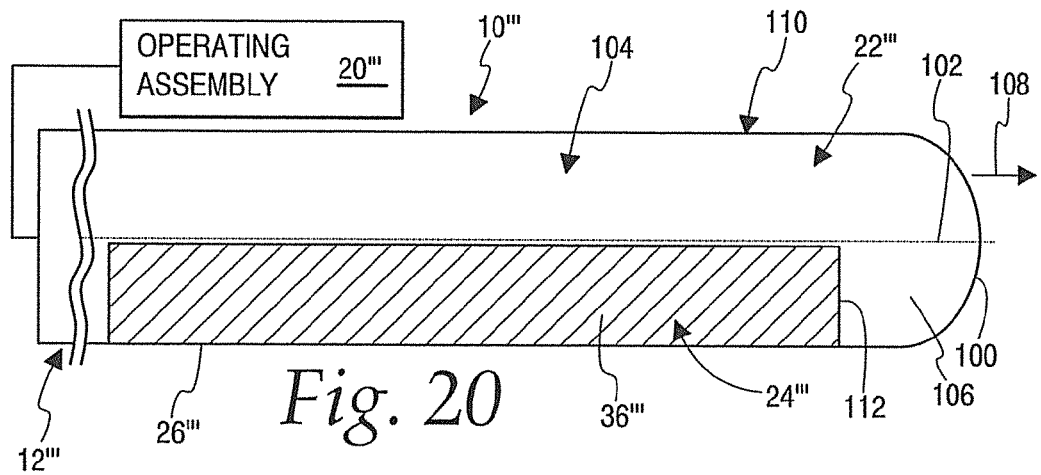
FIG. 20 is a fragmentary, elevation view of one specific form of medical instrument as depicted in FIG. 19.

One specific form of the medical instrument 10''' is shown in FIG. 20. The medical instrument 10''' has a frame 12''' with an associated operating assembly 20''', shown in schematic form, and a working assembly 22''' incorporating a tip 24'''.

The tip 24''' incorporates the cautery component 36''', in this case in the form of an elongate blade with a substantially straight operating edge 26''' with the line thereof extending generally parallel to a central axis 102 of the frame 12'''.

According to the invention, insulating material defines substantially the entire exposed surface 104 of the tip 24''', with the exception of that portion of the exposed surface area defined by the blade 36''' as required for it to be operational. The insulating material preferably makes up at least that portion of the tip 24''', and potentially the frame 12''', that become exposed to bodily tissue during a procedure. Conductive materials contiguous with, or in the vicinity of, the cautery component 36''' could conduct its generated current, directly or through bodily fluids, to surrounding tissues so as to potentially cause damage thereto. The insulating material provides an electrical barrier to inhibit such current conducting as might damage tissue, during introduction and/or while operating, the instrument 10'''.

In this embodiment, the tip 24''' has a body 106 that is generally cylindrical in cross-section with its axis coincident with the axis 102. As a result, the elongate frame 12''' and tip 24''' are substantially straight from a proximal region of the frame 12''' fully to the leading free end 100, in this case formed on the tip 24'''.

In this embodiment, substantially the entire area of the exposed surface 104 of the tip body 106, excluding the cautery component 36''', is made from the insulating material. As a result, as the medical instrument 10''' is introduced to a body cavity, as by movement in the direction of the arrow 108, the insulating material at the leading free end 100 will contact tissue and guide entry of the trailing portion of the medical instrument 10'''. The leading free end 100 is convex to facilitate this action.

Additionally with this construction, the insulating material makes up the portion of the body 106 at 110 that is diametrically opposite to the location of the edge 26'''. This portion 110 can be used to engage and reposition tissues to strategically situate the medical instrument 10''' preparatory to cauterization, without significant exposure of the tissue to the cautery component 36''', which may be activated as this movement occurs.

Further electrical insulation is achieved by situating the forward end 112 of the cautery component 36''' at a location spaced rearwardly from the leading free end 100.

While it is preferred to make the entire area of the exposed surface 104, excluding that made up by the cautery component 36''', of the insulating material, as an alternative, the insulating material can be more strategically utilized. For example, as shown in FIG. 26, the distal end of the body 106 made from insulating material may be capped with a conductive component 114 that defines the leading free end 100. With this arrangement, there is a region at 116 that electrically isolates the end 112 of the cautery component 36''' from the component 114. Thus, the same insulating effect is realized by placing the insulating material between the cautery component 36''' and the leading free end 100. As a result, current does not conduct from the cautery component 36''' to the leading free end 100 such that it might additionally conduct therethrough to body tissue during a medical procedure.

As noted previously, the tip 24''' is at all times fixed relative to the frame 12''' with this particular embodiment. It is conceivable that structure could be incorporated, such as that previously described or other structure, to allow reorientation of the tip 24'''.

As previously described, the nature of the insulating material is not critical to the present invention. As examples, the insulating material might be a plastic or other non-metal material, such as a composite, etc. The material is chosen so as not to freely conduct the current in a manner that could potentially damage contacted tissue.

Figure 21:
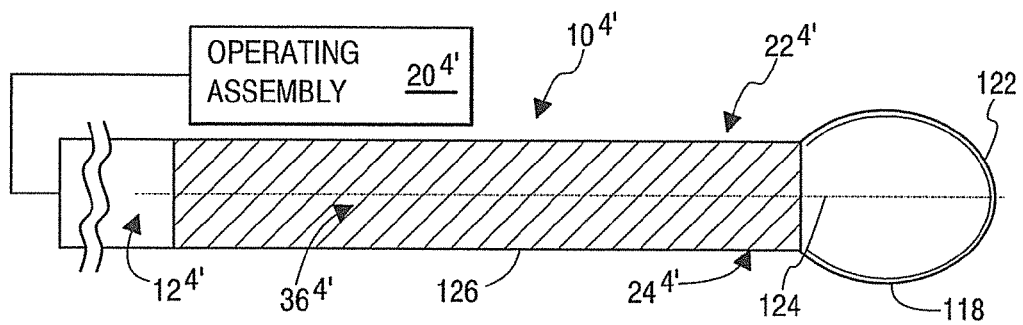
FIG. 21 is a view as in FIG. 20 of a further modified form of medical instrument, according to the invention.

In FIG. 21, a further modified form of medical instrument is shown at 10$^{4'}$. The medical instrument 10$^{4'}$ has a frame 12$^{4'}$ with a working assembly at 22$^{4'}$ at a distal region of the frame 12$^{4'}$. An operating assembly 20$^{4'}$ is incorporated at a proximal region of the frame 12$^{4'}$.

In this embodiment, the working assembly 22$^{4'}$ includes a tip 24$^{4'}$ with a cautery component 36$^{4'}$. The cautery component 36$^{4'}$ is fully exposed around the circumference of the tip

24⁴'. At the distal end of the cautery component 36⁴', another component 118 is incorporated into the tip 24⁴' and is constructed so that its exposed, external peripheral surface 124 is made from an insulating material. The component 118 has a convex leading free end 122. The component 118 extends radially relative to a central axis 124 for the frame 12⁴' and tip 24⁴' beyond the circumferential surface 126 of the cautery component 36⁴'.

Figure 22:
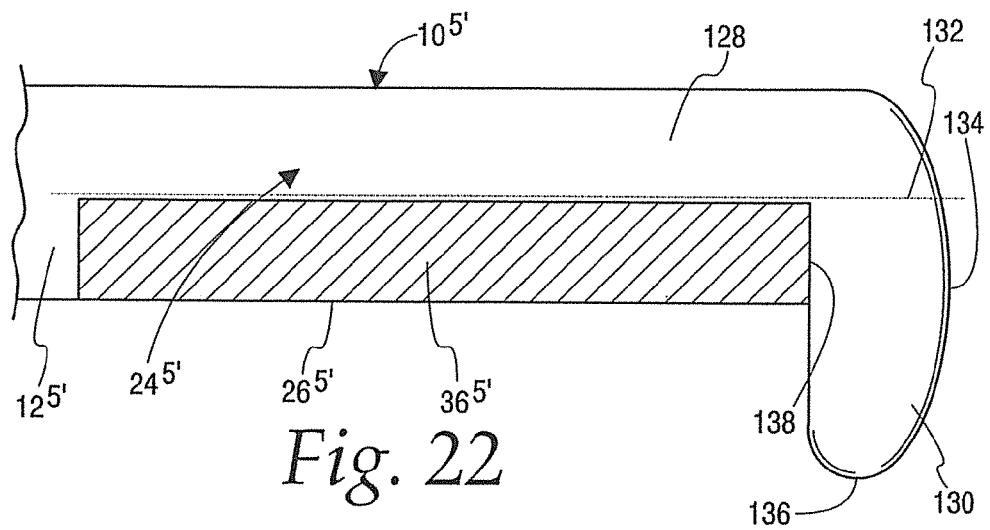
FIG. 22 is a view as in FIG. 21 of a further modified form of medical instrument, according to the invention.

In FIG. 22, a portion of a further modified form of medical instrument, according to the present invention, is shown at 10⁵'. In this embodiment, a tip 24⁵' defines by itself and/or with a part of an elongate frame 12⁵', an overall "L" shape. The "L" shape is defined by angled legs 128, 130, with the leg 128 having a length aligned with the central axis 132 of the frame 12⁵'.

The leg 130 has separate convex surfaces 134, 136 defining essentially separate leading free ends. The convex surface 134 defines the distalmost part of the medical instrument 10⁵'.

In this embodiment, the cautery component 36⁵' has a straight edge 26⁵' extending generally parallel to the axis 132. The edge 26⁵' extends up to the leg 130, which extends radially outwardly a substantial distance from the distal end 138 of the cautery component 36⁵', to effectively shield the same. Thus, the leg 130 is strategically situated to allow repositioning of tissue within a body cavity while additionally affording the electrically insulating barrier between the tissue and the cautery component 36⁵'.

Figure 23:
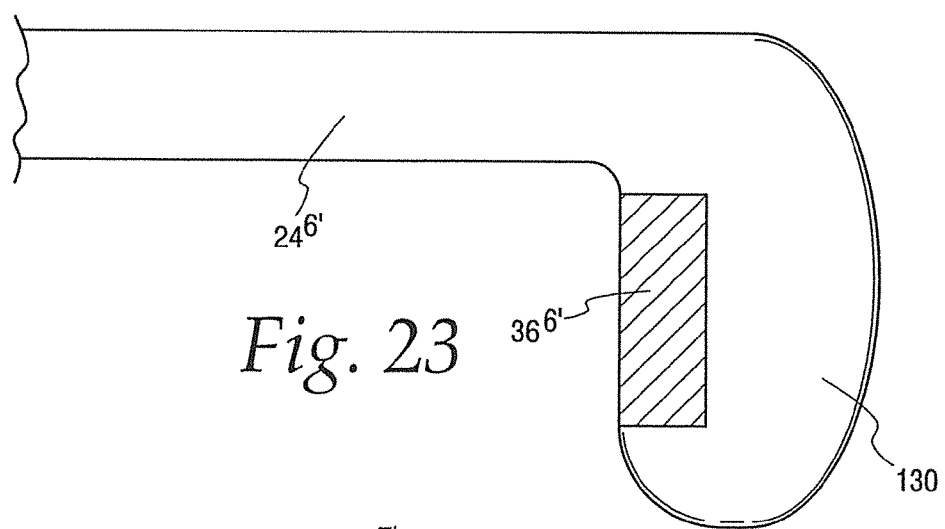
FIG. 23 is a view as in FIG. 22 of a further modified form of medical instrument, according to the invention.
Figure 24:
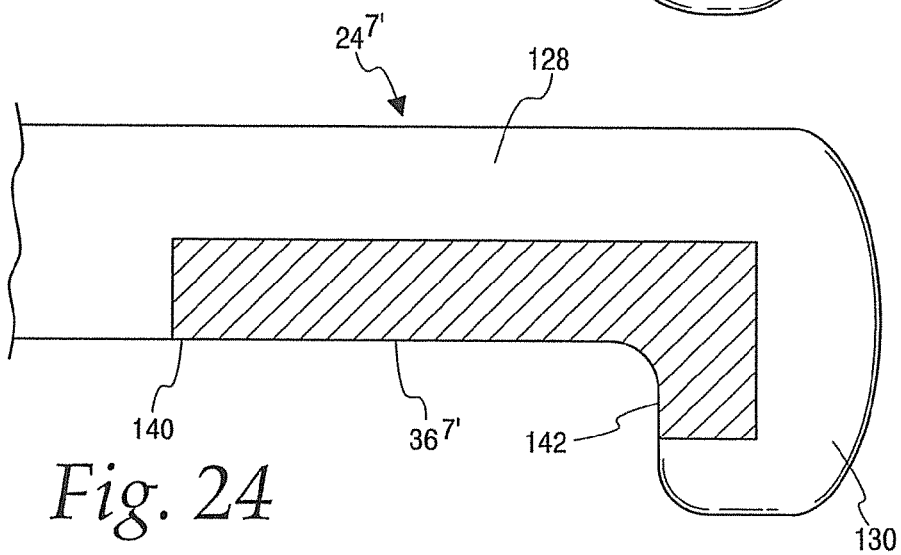
FIG. 24 is a view as in FIG. 23 of a further modified form of medical instrument, according to the invention.

FIGS. 23 and 24 show tips 24⁶', 24⁷', respectively, that are variations of the tip 24⁵'. The only difference in each is the configuration of the cautery component.

In FIG. 23, the cautery component 36⁶' is located on the leg 130, whereas on the tip 24⁷', the cautery component 36⁷' essentially combines the configurations of the cautery components 36⁵', 36⁶' to wrap around both legs 128, 130. Accordingly, the cautery component 36⁷' is made up of separate straight edge lengths 140, 142 that are angled with respect to each other.

In FIG. 25, a further form of medical instrument shown at 10⁸' that has a tip at 24⁸' that defines by itself, or in conjunction with a part of an elongate frame 12⁸', an overall "J" shape.

The "J" shape is defined by a base 144 and spaced long and short legs 146, 148, respectively. The base 144 has an exposed surface 149 with a convexly curved distalmost part thereon at 150 defining the leading free end of a tip 24⁸' on the medical instrument 10⁸'. The insulating material is provided between the surface part 150 and cautery component 36⁸'. In this embodiment, the cautery component 36⁸' is provided on the base 144. The cautery component itself may be extended, or additional cautery components may be provided, to form a cutting edge on one or both of the legs 146, 148.

With each of the embodiments in FIGS. 21-25, the exposed surfaces on each of the tips 24⁴'-24⁸' can be made substantially entirely, or strategically, from insulating material to control collateral damage due to current flow to the tissue in the region at which cauterization is carried out. The insulating material also allows the various medical instruments to be repositioned to move tissue within a cavity, as upon introduction of the instrument and/or to gain access to a particular site, while the cauterization component is energized without inflicting any appreciable damage.

With the above-described structures, a method can be carried out as shown in flow diagram form in FIG. 27.

As shown in block 152, a medical instrument is provided, as described above. As shown at block 154, the medical instrument is repositioned so that the distal end thereof is moved up to and into contact with a human body part at a cutting location. As shown at block 156, at least one cautery component is operated to alter the contacted human body part at the cutting location.

Preferably, the contact with tissue, other than that to be treated, occurs primarily through the insulating material, at least while the one or more cautery components are energized.

In FIG. 28, a further modified form of medical instrument is shown at 10⁹'. The medical 10⁹' is shown in schematic form to encompass embodiments as hereinafter described, as well as embodiments with variations of the basic components thereof and their interaction. The schematic representation is intended to encompass all of these constructions.

The medical instrument 10⁹' has an elongate frame 12⁹' with proximal and distal ends 200, 202, respectively, that are spaced in a lengthwise direction along a central axis of the frame 12⁹'.

A working assembly 22⁹' is provided at the distal region of the frame 12⁹', with an operating assembly 20⁹' at a proximal region of the frame 12⁹'.

The working assembly 22⁹' defines a cutting space 204 within which a cutting edge 206 is located. The cutting edge 206 is functional with or without a cauterization capability. As explained in greater detail below, the working assembly 22⁹' is configured to "hook" a tissue to be cut, as described for other embodiments above, and maneuver a part of the tissue into the cutting space 204 and against the cutting edge 206. The tissue passes through an entryway into the cutting space 204 and to against the cutting edge 206. The cutting edge 206 can be drawn against the tissue to effect cutting thereof.

Through at least one repositionable component 208, the dimensions of the entryway can be selectively changed to either fully block the entryway or change its dimension to control the volume of tissue that can pass therethrough and to against the cutting edge 206. The component(s) 208 can be manipulated remotely from the working assembly 22⁹', as by an actuator 210 on the operating assembly 20⁹'.

One specific exemplary form of the medical instrument 10⁹' is shown in FIGS. 29-32.

The elongate frame 12⁹' has the aforementioned proximal and distal ends 200, 202 spaced in a lengthwise direction along the central axis 212 of the frame 12⁹'.

The working assembly 22⁹' has a hooked/U-shaped portion 214 defined by first and second legs 216, 218 that meet at a base 220. The U-shaped portion 214 opens towards the proximal end of the elongate frame 12⁹' and defines a cutting space at 222 within which the tissue to be cut can be directed.

The working assembly 22⁹' further has a cutting assembly at 224 with at least one blade 226 with a sharp edge 228 that can be drawn against tissue to effect cutting thereof.

The working assembly 22⁹' and elongate frame 12⁹' are configured so that a tissue entryway 229 is defined between a distal end 230 of a straight length 232 of an elongate shaft 234 on the frame 12⁹' and a free end 236 of the first leg 216. Tissue is advanced through the entryway 229 into the cutting space 222 to against the sharp edge 228 whereupon drawing of the sharp edge 228 against the tissue effects its severance.

A first assembly 238 is configured to be operated to vary a configuration of the entryway 229. In this embodiment, the entire elongate shaft 234 has a straight configuration between the end 230 and a proximal end 240 thereof embedded in a handle 242. The elongate shaft 234 is concentric with the central axis 212. The first assembly 238 consists of at least the first component 208 that slides guidingly within the elongate shaft 234 back and forth in a path along the central axis 212. As this occurs, a width dimension W for the entryway 229, generally parallel to the central axis 212, is varied.

The component 208 and the actuator 210 attached thereto make up the first assembly 238. The actuator 210 is also part of the operating assembly $20^{9'}$. The actuator 210 is slidable guidingly axially within a slot 244 formed in the handle 242 and elongate shaft 234 between solid line and dotted line positions shown in FIG. 29. Preferably, the component 208 is fixed to the actuator 210 to follow its axial movement. With the actuator 210 in the solid line position in FIG. 29, a free end 246 of the component 208 is abutted, or closely adjacent, to the free end 236 of the first leg 216. In this position, the component 208 fully blocks the width W of the entryway 229.

By moving the actuator 210 from the solid line position into the dotted line position in FIG. 29, the actuator 210 draws the component 208 axially in a proximal direction to situate the free end 246 at the proximal, axial end of the entryway 229, thereby leaving the entryway 229 fully open. Shoulders 248, 250 are formed at the axial ends of the slot 244, thereby to block the actuator 210 as it moves the component 208 in its axial operating path between positions wherein the width of the entryway 229 is fully blocked and fully open/exposed. In between these positions, the entryway 229 has an intermediate width.

While not required, in the depicted and preferred form, the component 208 is in the form of an elongate rod that is concentric with the elongate shaft 234, with each component centered on the axis 212. With this arrangement, the proximal end of the elongate shaft 234 can be anchored in the handle 242, which can be conveniently grasped by a surgeon to access the actuator 210, as with the thumb on the grasping hand through which movement of the actuator 210 can be effected.

In this embodiment, the cutting blade 226 is configured so that the sharp edge 228 thereon conforms nominally to the curvature of the U-shaped portion 214. The cutting edge 228 extends approximately the same distance from the base along each of the legs 216, 218, terminating short of the free end 236 of the first leg 216. The primary cutting occurs where the cutting edge 228 extends over the base 220.

As with other embodiments described herein, the hooked/U-shaped portion 214 is configured to allow remote manipulation of tissue preparatory to cutting thereof. More specifically, the free end 236 of the first leg 216 is used to hook tissue and strategically reposition and maneuver it towards the entryway 229. Once the region to be cut is at the entryway 229, the working assembly $22^{9'}$ can be drawn against the tissue to first bring the tissue into the cutting space 204 and up to the cutting edge 228. Further pressure application causes the cutting edge 228 to sever the tissue.

To avoid inadvertent escape of the tissue from within the cutting space 222, once strategically placed therein, at least one discrete component is provided on at least one of the legs 216, 218 to inhibit sliding of the tissue against that particular leg. In this embodiment, a plurality of like, discrete components 252 is provided on the first leg 216. The components 252 are shown in the form of substantially parallel ribs, each tapering to an apex 254. The tapering ribs project angularly generally away from the free end 236 and press into the tissue so as to reduce the likelihood that tissue bearing on the first leg 216 and ribs 252 will slide relative to the first leg 216 within the cutting space 222 in a direction wherein the tissue might fall off of the free end 236 of the first leg 216. The apices 254/free ends may be sharpened to each, and cooperatively, grip tissue.

The ribs are preferably configured so as to limit tissue slippage but preferably do not engage in a manner that might damage the tissue as the medical instrument is separated from the tissue after severance.

The free end 236 of the first leg 216 is rounded/blunt so as not to readily cut through tissue bearing thereagainst as the tissue is engaged by the medical instrument $10^{9'}$ as it is being manipulated thereby.

In this embodiment, the first leg 216 has a projecting length from the base 220 extending along a line that is at an angle $\alpha$ with respect to the central axis 212. The angle is preferably around 45°±15°.

A transition section 256 connects between the elongate shaft 234 and second leg 218. The transition section 256 projects in a line at an angle $\alpha 1$ to the axis 212 that is less than the angle $\alpha$. The length of the transition section 256 is adequate to situate the free end 236 of the first leg 216 near the axis 212, with a slight projection therebeyond to be substantially flush with the perimeter edge 258 of the component 208.

The component 208 can be moved to the FIG. 29 position to place the medical instrument $10^{9'}$ in a state wherein introduction of the medical instrument $10^{9'}$ is facilitated without snagging of the working assembly $22^{9'}$ on the tissue. An optional cannula 260 can be used in conjunction with the medical instrument $10^{9'}$ as shown in FIGS. 29 and 30. The cannula 260 has an internal passage 262 within which at least part of the working assembly $22^{9'}$ can be placed with the cannula 260 and medical instrument $10^{9'}$ in a first relationship, as shown in FIG. 30. The cannula 260 and medical instrument $10^{9'}$ are movable relative to each other to change from the first relationship into a second relationship, as shown in FIG. 29, wherein at least a portion, and preferably the entirety of, the working assembly $22^{9'}$ is exposed outside of the cannula 260.

With the above-described construction, the U-shaped portion 214 is strategically oriented to allow comfortable and controlled repositioning of tissue through manipulation of the handle 242. The medical instrument $10^{9'}$ can be directed to an appropriate operating site with or without the cannula 260.

As an alternative to using the rib construction of FIG. 32, components 264, as shown in FIG. 33, might be utilized. The components 264 project angularly in the same manner as the ribs 252 but, rather than having extended apices, terminate at points 266. The components 264 otherwise function as the components 252 to reduce the likelihood of slippage of tissue along the leg upon which the components 252, 264 are provided.

Figure 35:
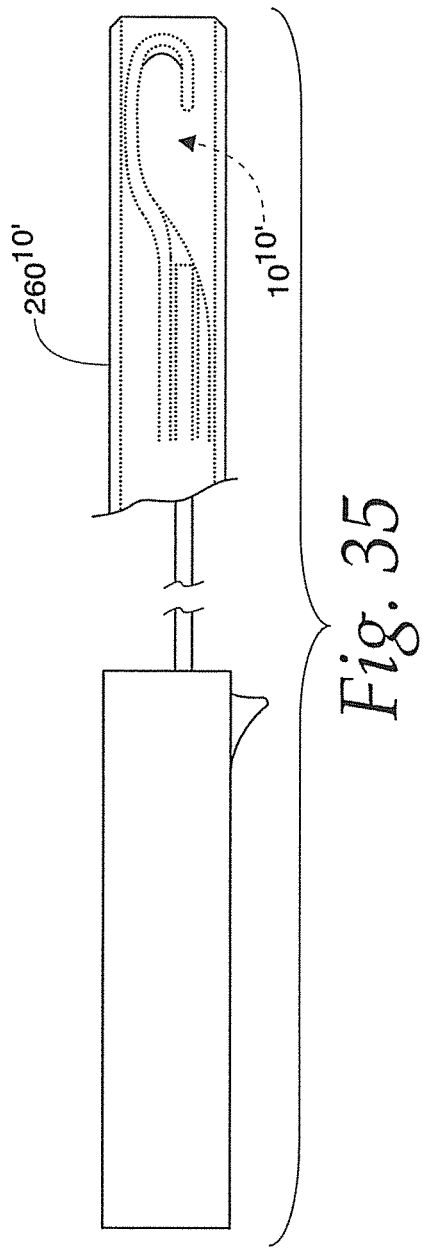
FIG. 35 is a view as in FIG. 34 wherein the state of the medical instrument has been changed to correspond to that shown in FIG. 30.

In FIGS. 34 and 35, a modified form of medical instrument, according to the invention, is shown at $10^{10'}$. The differences between the medical instruments $10^{10'}$ and $10^{9'}$ reside principally at the distal ends where the cutting space is defined. In the medical instrument $10^{10'}$, the cutting space $222^{10'}$ is bounded by first and second legs $216^{10'}$ and $218^{10'}$, corresponding to the legs 216, 218, respectively. A curved transition section $256^{10'}$ connects the elongate shaft $234^{10'}$ to the second leg $218^{10'}$.

In this embodiment, the first leg $216^{10'}$ projects in a line that is substantially parallel to the central axis $212^{10'}$ of the frame $12^{10'}$. As depicted, the line of the first leg $216^{10'}$ is adjacent to the central axis $212^{10'}$. The line of the first leg $216^{10'}$ may be coincident with the axis $212^{10'}$.

The second leg $218^{10'}$ projects in a line that is substantially parallel to that of the first leg $216^{10'}$ and the central axis $212^{10'}$. The transition section $256^{10'}$ curves in an arc around the cutting space $222^{10'}$ to meet the second leg $218^{10'}$.

An optional cannula $260^{10'}$ is depicted to function as the aforementioned cannula 260.

Figure 36:
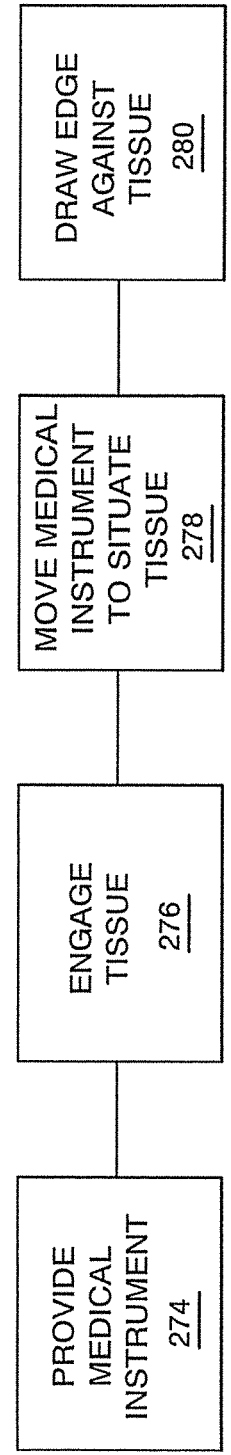
FIG. 36 is a flow diagram representation of a method, according to the present invention, for cutting a human tissue using the medical instruments in FIGS. 29-35.

The invention also contemplates a method of cutting a human tissue utilizing the medical instruments $10^{9'}$, $10^{10'}$. As shown in flow diagram form in FIG. 36, a medical instrument, as described above is provided, as shown at block 274.

As shown at block 276, the free end of the first leg of the instrument is engaged with tissue.

As shown at block 278, the medical instrument is moved relative to the tissue so that a part of the tissue is: a) moved into the cutting space and against the sharp edge of the cutting assembly; and b) engaged by at least one discrete component that resists sliding movement of the part of the tissue out of the cutting space. The method could also be practiced without the at least one discrete component.

As shown at block 208, with the tissue against the sharp edge, the sharp edge is drawn against the part of the tissue to effect cutting thereof.

The foregoing disclosure of specific embodiments is intended to be illustrative of the broad concepts comprehended by the invention.

The invention claimed is:

1. A medical instrument comprising:
   an elongate frame with proximal and distal ends spaced in a lengthwise direction along a central axis of the frame;
   a working assembly at a distal region of the frame,
   the working assembly comprising a U-shaped portion defined by first and second legs meeting at a base,
   the U-shaped portion opening toward the proximal end of the elongate frame and defining a cutting space,
   the working assembly further comprising a cutting assembly with a sharp edge at a fixed location in the cutting space to be urged against a tissue through manipulation of the frame to effect cutting thereof,
   the working assembly and elongate frame configured so that a tissue entryway is defined through which a tissue can be advanced to be moved into the cutting space and against the sharp edge; and
   the medical instrument further comprising a first assembly configured to be operated to vary a configuration of the entryway.

2. The medical instrument according to claim 1 wherein the entryway has a width dimension substantially parallel to the central axis of the frame and the first assembly is configured to vary the width of the entryway.

3. The medical instrument according to claim 2 wherein the first assembly comprises a first component that is advanced in a direction substantially parallel to the central axis of the frame to vary the width of the entryway.

4. The medical instrument according to claim 3 wherein the medical instrument further comprises an operating assembly with an actuator on the frame at a location spaced from the working assembly towards a proximal end of the frame, the actuator configured so as to be operable to move the first component in an operating path in opposite directions substantially parallel to the central axis of the frame.

5. A medical instrument comprising:
   an elongate frame with proximal and distal ends spaced in a lengthwise direction along a central axis of the frame;
   a working assembly at a distal region of the frame,
   the working assembly comprising a U-shaped portion defined by first and second legs meeting at a base,
   the U-shaped portion opening toward the proximal end of the elongate frame and defining a cutting space,
   the working assembly further comprising a cutting assembly with a sharp edge in the cutting space to be pressed against a tissue to effect cutting thereof,
   the working assembly and elongate frame configured so that a tissue entryway is defined through which a tissue can be advanced to be moved into the cutting space and against the sharp edge; and
   the medical instrument further comprising a first assembly configured to be operated to vary a configuration of the entryway,
   wherein the entryway has a width dimension substantially parallel to the central axis of the frame and the first assembly is configured to vary the width of the entryway,
   wherein the first assembly comprises a first component that is advanced in a direction substantially parallel to the central axis of the frame to vary the width of the entryway,
   wherein the first leg of the U-shaped portion has a free end and the first component is advanced selectively towards and away from the free end of the first leg to respectively decrease and increase the width of the entryway.

6. The medical instrument according to claim 5 wherein the first component has a free end that can be moved to reside at or adjacent to the free end of the first leg to substantially block the width of the entryway.

7. The medical instrument according to claim 5 wherein the first component is in the form of an elongate rod with an axis that is substantially parallel to the central axis of the frame.

8. The medical instrument according to claim 5 wherein the first leg projects in a line that is substantially parallel to the central axis of the frame, the line one of: a) coincident with; or b) adjacent to the central axis of the frame.

9. The medical instrument according to claim 1 wherein the cutting edge is located at the base of the U-shaped portion.

10. The medical instrument according to claim 1 wherein the first and second legs project in substantially parallel lines that are substantially parallel to the central axis of the frame.

11. The medical instrument according to claim 1 wherein at least one discrete component is provided on at least one of the first and second legs and configured to inhibit sliding of tissue against and along the at least one of the first and second legs.

12. A medical instrument comprising:
   an elongate frame with proximal and distal ends spaced in a lengthwise direction along a central axis of the frame;
   a working assembly at a distal region of the frame,
   the working assembly comprising a U-shaped portion defined by first and second legs meeting at a base,
   the U-shaped portion opening toward the proximal end of the elongate frame and defining a cutting space,
   the working assembly further comprising a cutting assembly with a sharp edge in the cutting space to be pressed against a tissue to effect cutting thereof,
   the working assembly and elongate frame configured so that a tissue entryway is defined through which a tissue can be advanced to be moved into the cutting space and against the sharp edge; and
   the medical instrument further comprising a first assembly configured to be operated to vary a configuration of the entryway,
   wherein at least one discrete component is provided on at least one of the first and second legs and configured to inhibit sliding of tissue against and along the at least one of the first and second legs,
   wherein the one of the first and second legs has a free end and the one discrete component projects away from the free end.

13. A medical instrument according to claim 12 wherein the at least one discrete component has a sharp free end.

14. A medical instrument comprising:
   an elongate frame with proximal and distal ends spaced in a lengthwise direction along a central axis of the frame;
   a working assembly at a distal region of the frame,
   the working assembly comprising a U-shaped portion defined by first and second legs meeting at a base, the U-shaped portion opening toward the proximal end of the elongate frame and defining a cutting space, the working assembly further comprising a cutting assembly with a sharp edge in the cutting space to be pressed against a tissue to effect cutting thereof, the working assembly and elongate frame configured so that a tissue entryway is defined through which a tissue can be advanced to be moved into the cutting space and against the sharp edge; and the medical instrument further comprising a first assembly configured to be operated to vary a configuration of the entryway, wherein at least one discrete component is provided on at least one of the first and second legs and configured to inhibit sliding of tissue against and along the at least one of the first and second legs, wherein the at least one discrete component comprises a pair of spaced ribs.

15. The medical instrument according to claim 1 in combination with a cannula with an internal passage within which at least a part of the working assembly resides with the cannula and medical instrument in a first relationship, the cannula and medical instrument movable relative to each other to change from the first relationship into a second relationship wherein at least a portion of the part of the working assembly is exposed outside of the cannula.

16. The medical instrument according to claim 1 wherein the frame has an elongate shaft with a first length that is substantially parallel to the central axis, the central axis of the frame extending through the elongate shaft, and a transition section connects between the first length and second leg.

17. The medical instrument according to claim 1 wherein the free end of the first leg is blunt so as not to readily cut through tissue bearing against the end of the first leg as tissue is engaged and manipulated by the medical instrument.

18. The medical instrument according to claim 1 wherein the sharp edge on the cutting assembly has a curved shape.

19. The medical instrument according to claim 1 wherein the first leg projects in a straight line that makes an angle of between 30° and 60° with the central axis of the frame.

20. A method of cutting a human tissue, the method comprising the steps of:
  providing the medical instrument of claim 11;
  engaging the free end of the first leg with the tissue;
  progressively moving the medical instrument relative to the tissue so that part of the tissue is: a) moved into the cutting space and against the sharp edge of the cutting assembly; and b) engaged by the at least one discrete component so that the at least one discrete component resists sliding movement of the part of the tissue out of the cutting space; and
  with the tissue against the sharp edge, drawing the sharp edge against the part of the tissue to effect cutting thereof.

21. The medical instrument according to claim 7 wherein the rod has a diameter around the rod axis that is substantially less than a diameter of the elongate frame around the central axis of the frame.

* * * * *

UNITED STATES PATENT AND TRADEMARK OFFICE
CERTIFICATE OF CORRECTION

Page 1 of 1

PATENT NO. : 9,186,168 B2
APPLICATION NO. : 14/494118
DATED : November 17, 2015
INVENTOR(S) : Stien et al.

It is certified that error appears in the above-identified patent and that said Letters Patent is hereby corrected as shown below:

On the title page item [73], insert

--Stewart and Stien Enterprises, LLC,
Eau Claire, WI (US)--

Signed and Sealed this
First Day of March, 2016

Michelle K. Lee
*Director of the United States Patent and Trademark Office*